United States Patent [19]

Malhotra

[11] Patent Number: 4,539,039

[45] Date of Patent: Sep. 3, 1985

[54] HERBICIDAL (-3-FLUORO-5-TRIFLUOROMETHYL-PYRIDYL)OXY PHENYLOXIME DERIVATIVES

[75] Inventor: Sudarshan K. Malhotra, Walnut Creek, Calif.

[73] Assignee: The Dow Chemical Company, Midland, Mich.

[21] Appl. No.: 604,257

[22] Filed: Apr. 26, 1984

[51] Int. Cl.$^3$ .................. C07D 213/64; C07D 213/70; C07D 213/74; A01N 43/40
[52] U.S. Cl. ........................................ 71/94;.546/300; 546/288; 546/289; 546/309; 546/312
[58] Field of Search .................... 71/94; 546/300, 288, 546/289, 309, 312

[56] References Cited

U.S. PATENT DOCUMENTS

| | | |
|---|---|---|
| 4,308,053 | 12/1981 | Cartwright et al. ................... 71/94 |
| 4,322,241 | 3/1982 | Pissiotas et al. ....................... 71/94 |
| 4,329,167 | 5/1982 | Rempfler et al. ...................... 71/94 |
| 4,394,157 | 7/1983 | Pissiotas et al. ....................... 71/94 |
| 4,394,158 | 7/1983 | Pissiotas et al. ....................... 71/94 |
| 4,394,159 | 7/1983 | Buck et al. ............................. 71/94 |
| 4,420,328 | 12/1983 | Rempfler et al. ...................... 71/94 |
| 4,425,156 | 1/1984 | Pissiotas et al. ....................... 71/94 |
| 4,443,247 | 4/1984 | Rempfler et al. ...................... 71/94 |

Primary Examiner—Henry R. Jiles
Assistant Examiner—Dale A. Bjorkman

[57] ABSTRACT

Novel compounds, e.g., methyl (((1-(5-((fluoro-5-(trifluoromethyl)-2-pyridinyl)oxy)-2-nitrophenyl)ethylidene)amino)oxy)acetate which are selective herbicides useful for controlling weeds in valuable crops.

6 Claims, No Drawings

HERBICIDAL (-3-FLUORO-5-TRIFLUOROMETHYL-PYRIDYL-)OXY PHENYLOXIME DERIVATIVES

BACKGROUND OF THE INVENTION

An active area of agricultural research is devoted to the production of more productive plant life, especially that plant life associated with food sources for man. One aspect of that research is the search for more efficient and more selective herbicides to control undesired vegetation in the presence of valuable crops, thereby reducing the competition for water, sunlight and nutrients and increasing yields.

DESCRIPTION OF THE PRIOR ART

U.S. Pat. No. 4,308,053 describes and claims certain phenoxypyridines and their use as herbicides, e.g., 2-(3-carboxyphenoxy)-3-chloro-5-trifluoromethylpyridine. Copending application Ser. No. 380,840, filed June 18, 1982, describes and claims certain fluoro-substituted pyridyl(oxy/thio)phenoxy compounds having herbicidal activity. Other related compounds are disclosed and claimed in U.S. Pat. Nos. 4,322,241; 4,394,157; 4,394,158; 4,425,156 in copending application Ser. No. 434,994 filed on Oct. 18, 1982 and in copending application Ser. No. 506,135 filed June 20, 1983.

SUMMARY OF THE INVENTION

The present invention is directed to novel compounds having herbicidal activity which correspond to the formula

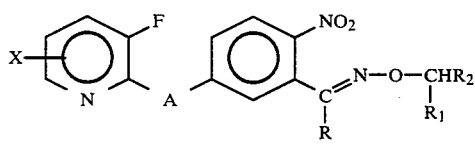

wherein
- X is independently $CF_3$, $CHF_2$, $CClF_2$, Br, Cl, I, F, CN, $CHCl_2$, $CCl_3$ or $CCl_2F$;
- A is O, S, NH or N-alkyl;
- R and $R_1$ are independently hydrogen, lower alkyl or halogen; and
- $R_2$ is an organic moiety containing N, O or S atoms or a metallic, ammonium or organic amine cation, and is or can be hydrolyzed and/or oxidized in plants or soil to a carboxyl moiety that is in undissociated and/or dissociated form, and their stereospecific isomers.

$R_2$ moieties include, but are not limited to moieties corresponding to one of the following formulae:

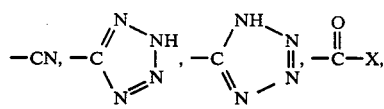

wherein X is halogen, or CN,

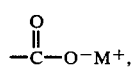

wherein M is a metallic cation, ammonium or an organic amine cation typically, but not exclusively, containing alkyl (saturated or unsaturated), alicyclic, heterocyclic or aromatic groups, all unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl,

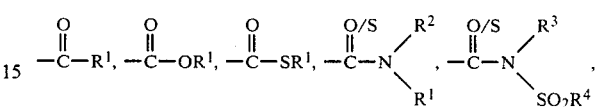

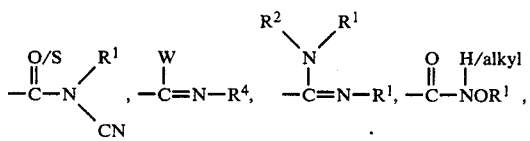

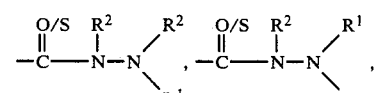

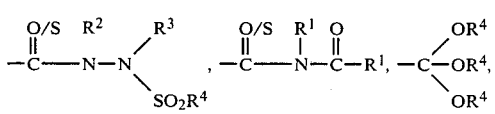

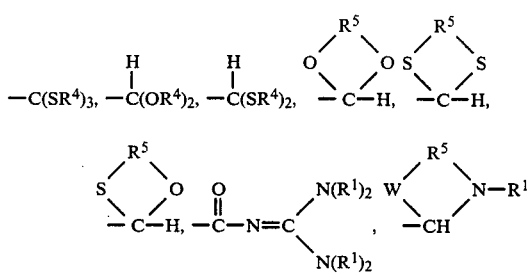

where W is S or O, where W is halogen or a group having the formula $-NHR^4$, $N(R^4)_2$, $OR^4$ or $SR^4$ wherein $R^4$ is identified as described hereinafter; $R^1$ is H or $R^4$; $R^2$ is H, alkoxy or $R^4$; $R^3$ is H, a metallic cation or $R^4$; and $R^4$ is an alkyl (saturated or unsaturated), alicyclic, heterocyclic or aromatic group, unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl,

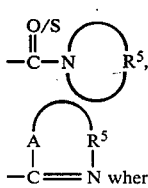

—C≡N where A is O, S or N, or

-continued

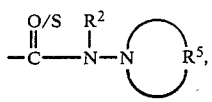

where $R^5$ completes an unsubstituted or substituted saturated heterocyclic ring system.

The above derivatives can be made by processes generally known to those skilled in the art and as described in the above-mentioned patents. For example, the corresponding acid chlorides can be reacted with a Grignard reagent to make the desired aldehyde or ketone derivative. Similarly, reaction of an acid chloride with KSH will provide the desired thiol acid. Thioamides may be prepared from the corresponding amide by reaction with $P_2S_5$ or, if hydrogen is present on the nitrogen atom, the carbonyl may be converted to, e.g., chloride, with removal of HCl, followed by reaction with hydrogen sulfide. Carbamoyl chlorides are available in the art or they may be prepared from the desired amine and phosgene or thiophosgene for use in making compounds containing the

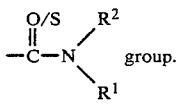

group.

The reaction of an amine with a sulfonyl chloride, e.g., $R^3NH_2 + R^4SO_2Cl$ provides the group

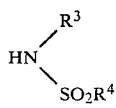

for use in reacting with an appropriate acid chloride.

The reaction of an amine with BrCN provides, e.g.,

which reacts with the appropriate acid chloride to provide compounds containing the

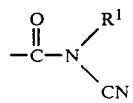

moiety. $P_2S_5$ is employed to make the corresponding S-containing compound.

Reaction of the above cyanoamine with phosgene or thiophosgene provides

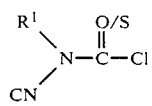

for use in making the corresponding derivatives.

The reaction of the compounds having the moiety

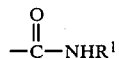

with $PCl_5$ will provide compounds having the moiety

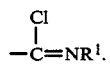

The reaction of the corresponding acid chloride with $RONH_2$ will provide compounds having the group

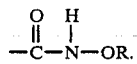

Most preferably $R_2$ is:

wherein Z is lower alkyl, preferably methyl.

In the formula for the aforementioned novel compounds, X is preferably 5-$CF_3$, A is preferably O, R is preferably hydrogen, $R_1$ is preferably H and $R_2$ is preferably $CO_2Z$ wherein Z is lower alkyl of 1 to 4 carbon atoms. Most preferably Z is methyl.

The compounds of formula (I) are useful both as pre- and postemergence broadleaf herbicides, especially in the presence of soybeans and corn. Preemergence herbicides are usually used to treat the soil in which a crop is to be planted, by application before or during seeding, or after seeding and before the crop emerges. Postemergence herbicides are applied after the crop plants have emerged from the soil. Compounds of formula (I) may be used as selective herbicides in a variety of crops including, for example, cotton, soya bean, peanuts, sugar beet, peas, wheat, barley and rice. They may also be used as total herbicides. They may be applied by any of the conventional techniques for applying herbicides. When applied as preemergence herbicides they may, for example, be sprayed on the surface of the soil before or during seeding, or after seeding and before emergence of the crop. In some situations, for example, in preemergence application to soya bean crops it may be advantageous to incorporate the compound of the invention into the soil before planting the crop. This may be done by applying the compound to the surface of the soil and then discing or harrowing the soil to mix the compound with the soil. Alternatively, use may be made of the applicators which have been developed for placing herbicides in a band beneath the surface of the soil.

The compounds of formula (I) may be combined with selective herbicides to achieve broadspectrum weed control in crops, for example, crops of soybean, cotton and peas. Alternatively, the second herbicide component may be a nonselective herbicide chosen to enhance the power of the compound of formula I as a total vegetation control herbicide.

Examples of herbicides for use in admixture with compounds of formula (I) include, but are not restricted to, the following:

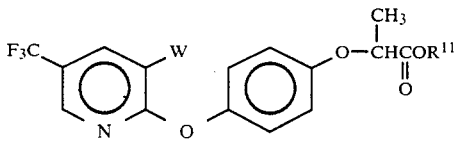

where W is H, Cl or F, and $R^{11}$ is a carboxylic acid or a salt, ester, thioester or amide thereof.

The compounds employed in the method of the present invention are novel compounds and may be prepared using the requisite starting materials by known procedures such as described in the aforementioned prior art and as illustrated in the following examples:

EXAMPLE 1

Preparation of 1-(3-((3-fluoro-5-(trifluoromethyl)-2-pyridinyl)oxy)phenyl ethanone A mixture of 1.83 grams (g) of 2,3-difluoro-5-(trifluoromethyl)pyridine, 1.36 g of m-hydroxyacetophenone and 1.4 g of $K_2CO_3$ in 25 ml of dimethylsulfoxide (DMSO) was stirred at room temperature overnight. Water was added and the resulting mixture was extracted with ether. The ether extract was washed with water, dried over anhydrous magnesium sulfate ($MgSO_4$) and concentrated to a yellow oil which solidified on standing at ambient temperature. The solid was triturated with hexane and filtered, yielding a yellow crystalline material, m.p. 65°–67° C., 1.75 g. The structure was confirmed by NMR.

| Analysis: | C | H | N |
| --- | --- | --- | --- |
| Calculated | 56.19 | 3.01 | 4.68 |
| Found | 55.79 | 2.82 | 4.72 |

EXAMPLE 2

Preparation of 1-(5-((3-fluoro-5-(trifluoromethyl)-2-pyridinyl)oxy)-2-nitrophenyl) ethanone A mixture of 3 ml of concentrated $H_2SO_4$ and 1.5 ml of red fuming nitric acid was cooled in an ice bath and 1 g of the ethanone prepared above was added with stirring over a period of 10 minutes. The reaction mixture was quenched with ice and extracted with ether. The ether extract was washed with water, dried over anhydrous $MgSO_4$ and concentrated to a yellow oil. NMR indicated the oil to be the desired product.

| Analysis: | C | H | N |
| --- | --- | --- | --- |
| Calculated | 48.84 | 2.33 | 8.14 |
| Found | 47.56 | 2.32 | 8.72 |

EXAMPLE 3

Preparation of 1-(5-(3-fluoro-5-(trifluoromethyl)-2-pyridinyl)oxy)-2-nitrophenyl)ethanoneoxime A mixture of 2.5 g of the product from Example 2, 2 g of hydroxylaminehydrochloride and 3 g of $K_2CO_3$ in 100 ml of 95% ethanol was heated for 5 hours at reflux. The reaction mixture was diluted with water and extracted with ether. The ether extract was washed with water, dried over anhydrous $MgSO_4$ and concentrated under reduced pressure, affording a deep yellow oil shown to be the desired product by NMR. Yield was 1.2 g.

EXAMPLE 4

Preparation of methyl (((1-(5-((fluoro-5-(trifluoromethyl)-2-pyridinyl)oxy)-2-nitrophenyl)ethylidene)amino)oxy)-acetate A mixture of 1.1 g of the oxime prepared in Example 3, 0.6 g of methyl bromoacetate and 0.6 g of $K_2CO_3$ in 25 ml of DMSO was stirred at ambient temperature for 5 hours at which time gas chromatography indicated the disappearance of most of the starting oxime. The reaction mixture was diluted with water and extracted with ether. The ether extract was washed with water, dried over anhydrous $MgSO_4$ and concentrated under reduced pressure. The resulting oil was placed in a Kugelrohr and distilled to remove impurities boiling at 140°–145° C. @ 0.5 mm Hg. The residue, a brown oil, was shown to be the desired product by NMR and IR. $\eta R$ @ 25° C.=1.5244. Yield 0.9 g.

| Analysis | C | H | N |
| --- | --- | --- | --- |
| Calculated | 47.33 | 3.02 | 9.74 |
| Found | 47.67 | 3.09 | 9.46 |

Employing the above procedures and methods analogous to those in the described prior art and utilizing the appropriate starting materials, the following compounds may be prepared:

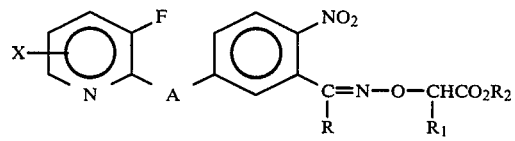

| | X | A | R | $R_1$ | $R_2$ |
| --- | --- | --- | --- | --- | --- |
| 1 | $CF_3$ | O | $C_2H_5$ | H | $CH_3$ |
| 2 | $CF_3$ | O | $CH_3$ | H | $C_2H_5$ |
| 3 | $CF_3$ | O | $CH_3$ | H | $CH_3$ |
| 4 | $CF_3$ | O | $CH_3$ | H | ipr |
| 5 | $CF_3$ | O | $CH_3$ | H | H |
| 6 | $CF_3$ | S | $CH_3$ | H | $CH_3$ |
| 7 | $CF_3$ | O | $C_2H_5$ | $CH_3$ | $CH_3$ |
| 8 | $CF_3$ | O | $C_2H_5$ | $CH_3$ | $C_2H_5$ |
| 9 | Cl | O | $CH_3$ | H | $CH_3$ |
| 10 | F | O | $CH_3$ | H | $C_2H_5$ |
| 11 | Br | O | $CH_3$ | $CH_3$ | $CH_3$ |
| 12 | F | O | $CH_3$ | H | $CH_3$ |
| 13 | Br | O | $CH_3$ | H | $C_2H_5$ |
| 14 | $CHF_2$ | O | $CH_3$ | H | $C_2H_5$ |
| 15 | $CHCl_2$ | O | $CH_3$ | H | $C_2H_5$ |
| 16 | $CF_3$ | NH | $CH_3$ | H | $CH_3$ |
| 17 | $CF_3$ | N-CH$_3$ | $CH_3$ | H | $CH_3$ |

The compounds utilized in the method of the present invention provide selective control of broad leaved weeds in valuable crops and give particular and advantageous selective postemergent control of such weeds.

For such uses, unmodified active ingredients of the present invention can be employed. However, the present invention embraces the use of the compounds in composition form with an inert material known in the art as an agricultural adjuvant or carrier in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or a different pesticidal use or as an additament. The compounds in combination can generally be present in the ratio of from 1 to 100 parts of the compound of the present invention with from 100 to 1 parts of the additional compound(s).

The exact rate to be applied is dependent not only on a specific active ingredient being applied, but also on a particular action desired, the plant species to be modified and the stage of growth thereof as well as the part of the plant to be contacted with the toxic active ingredient. Thus, all of the active ingredients of the present invention and compositions containing the same may not be equally effective at similar concentrations or against the same plant species.

In selective postemergent operations a dosage of about 0.01 to about 20 pounds/acre (0.0112–2.24 kg/hectare) is generally applicable, although not all compounds are equally effective and some weeds are more difficult to control.

The following examples illustrate the effects of the compounds of this invention. Under the conditions employed in these examples, a dosage of 1000 ppm roughly equates to 2.5 lbs/acre.

EXAMPLE 5

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to a 2–4 leaf stage in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species, test compound and dosage and the percent postemergent control obtained are set forth in Table I below. Control refers to the reduction in growth compared to the observed results of the same untreated specie.

Plant species in these tests were:

| Common Name | Scientific Name |
| --- | --- |
| Cotton | Gossypium nirsutum |
| Corn | Zea mays |
| Rape | Brassica napus |
| Soybeans | Glycine max |
| Morning Glory | Ipomoea spp. |
| Jimson Weed | Datura stramonium |
| Pigweed | Amaranthus spp. |
| Cocklebur | Xanthium spp. |
| Crabgrass | Digiteria spp. |
| Johnson grass | Sorghum halepense |
| Barnyard grass | Echinochloa crusgalli |
| Wild oats | Avena fatua |
| Yellow Foxtail | Setaria lutescens |
| Yellow Nutsedge | Cyperus esculentus |

TABLE 1

POSTEMERGENT CONTROL OF PLANT SPECIES

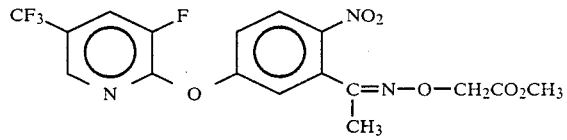

| Species | Percent Control At Indicated Application Rates (ppm) | | | | | |
| --- | --- | --- | --- | --- | --- | --- |
| | 125 | 62.5 | 31.25 | 15.6 | 7.8 | 3.9 |
| Corn | 25 | 25 | 20 | 10 | 10 | 0 |
| Soybeans | 10 | 10 | 0 | NT | NT | NT |
| Morning Glory | 99 | 100 | 100 | 80 | 40 | 20 |
| Pigweed | 100 | 100 | 100 | 100 | 95 | 70 |
| Jimson Weed | 100 | 100 | 100 | 100 | 100 | 80 |
| Cocklebur | 95 | 100 | 100 | 100 | 70 | 70 |
| Yellow Foxtail | 95 | 90 | 90 | 50 | 40 | 10 |
| Johnson grass | 80 | 70 | 80 | 20 | 0 | NT |
| Velvet Leaf | 100 | 100 | 85 | 60 | 30 | 20 |
| Barnyardgrass | 80 | 80 | 80 | 70 | 20 | 0 |
| Yellow Nutsedge | 80 | 80 | 60 | 40 | 20 | 10 |

EXAMPLE 6

So as to clearly illustrate the phytotoxic properties of the various active ingredients of the present invention applied preemergently, a controlled greenhouse experiment is described below.

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment the seed beds were maintained for two weeks under greenhouse conditions conducive for good plant growth and watered as necessary. The specific plant species, test compound, and dosage and the percent preemergent control are set forth in the table below. Control refers to the reduction in growth compared to the observed results of the same untreated species.

I claim:

1. A compound having the formula

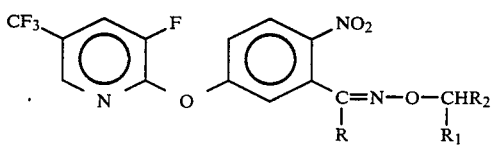

wherein R and R₁ are independently hydrogen or lower alkyl and R₂ is CO₂Z where Z is lower alkyl.

2. Compound of claim 1 having the formula

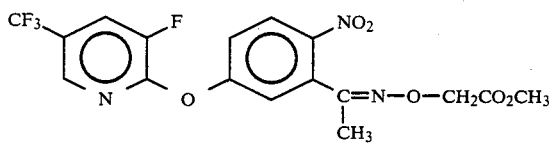

3. A composition comprising a carrier and a herbicidally effective amount of a compound having the formula

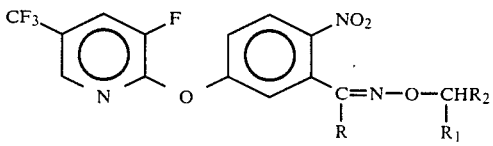

wherein R and R₁ are independently hydrogen or lower alkyl and R₂ is CO₂Z where Z is lower alkyl.

4. Composition of claim 3 wherein the compound has the formula

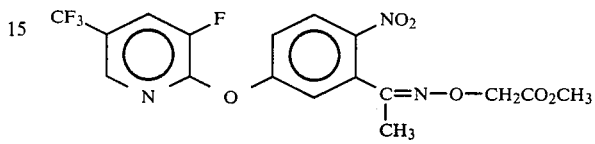

5. The method of controlling undesired plant growth in the presence of soybeans which comprises applying to the locus of said soybeans a herbicidally effective amount of a compound having the formula

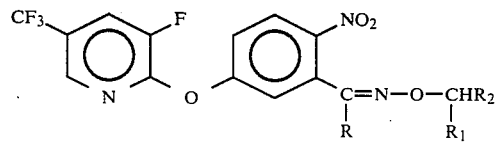

wherein R and R₁ are independently hydrogen or lower alkyl and R₂ is CO₂Z where Z is lower alkyl.

6. Method of claim 5 wherein the compound has the formula

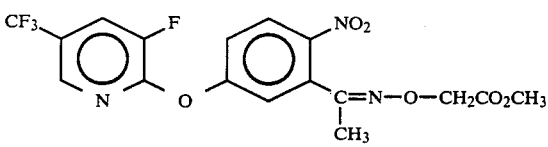

* * * * *